US00PP20033P2

(12) United States Plant Patent
Stommel et al.

(10) Patent No.: US PP20,033 P2
(45) Date of Patent: May 26, 2009

(54) ORNAMENTAL PEPPER NAMED '05C69-12'

(50) Latin Name: *Capisum annuum*
Varietal Denomination: 05C69-12

(75) Inventors: John R. Stommel, Glenwood, MD (US); Robert J. Griesbach, Ellicott City, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/006,521

(22) Filed: Jan. 3, 2008

(51) Int. Cl.
*A01H 5/00* (2006.01)

(52) U.S. Cl. ..... Plt./263.1
(58) Field of Classification Search ..... Plt./263.1, Plt./263
See application file for complete search history.

*Primary Examiner*—Annette H Para
(74) *Attorney, Agent, or Firm*—John D. Fado; G Byron Stover

(57) ABSTRACT

The present invention is a new and distinct pepper plant known as *Capisum annuum L.* '05C69-12' which displays a contrasting mixture of immature black and mature orange fruit at the same time unlike that of the standard pepper plants. Plants of '05C69-12' are characterized by greenish black foliage and numerous small tabasco shaped, upright oriented, solitary black fruits that mature orange.

3 Drawing Sheets

Genus and species of the claimed plant: *Capisum annuum.*
Variety denomination: '05C69-12'.

FIELD OF THE INVENTION

This invention concerns a new and distinct pepper plant known as *Capisum annuum L.* '05C69-12'.

DESCRIPTION OF RELATED PRIOR ART

Several commercial ornamental peppers are known. Ornamental peppers range in size and shape from short, compact plants with piquin sized fruits, such as 'Holiday Cheer', to plants as tall as 1 meter with full sized fruits, such as 'NuMex Mirasol'. Nearly all ornamental peppers have been primarily developed based upon unique fruit characteristics. '05C69-12' may be distinguished from all of the ornamental peppers known to us based upon its unique contrasting mixed display on the same aged plant of immature black and mature orange tabasco shaped fruit and greenish black foliage. Other peppers may display immature and mature fruit at the same time, such as 'Bolivian Rainbow', but do not have the unique combination of black and orange tabasco shaped fruit on greenish black foliage.

The characteristics of '05C69-12' were compared to the most similar plant on the market—'Ember' (not protected). 'Ember' plants have a smaller height to diameter ratio (0.60) and average 36 cm in diameter and 22 cm in height. 'Ember' has similar shaped (simple, entire, symmetrical, and lanceolate with an apiculate tip), sized (average 4.6 cm in length and 2.2 cm in width) and colored leaves (adaxial leaf surface is green) Royal Horticultural Society Colour Chart number 132C, mottled with black, Royal Horticultural Society Colour Chart number 202A, highlights). Flowers of 'Ember' are similar to '05C69-12' flowers in color (Royal Horticultural Society Colour Chart number 81A) and size (average 2.7 cm in diameter). Fruit of 'Ember' are similar in shape to '05C69-12' fruit but have different immature and mature fruit color. 'Ember' fruit are tabasco shaped and borne in clusters of 3 to 5. 'Ember' fruit average 3.0 cm in length, 0.8 cm in width at the midpoint, and 0.8 cm in width at the calyx. Immature 'Ember' fruit color is purple (Royal Horticultural Society Colour Chart number 79A) and mature fruit color is red (Royal Horticultural Society Colour Chart number 34A).

ORIGIN OF THE NEW PLANT

The new pepper plant originated from a controlled cross at the United States Department of Agriculture's Agricultural Research Service greenhouses in Beltsville, Md. '05C69-12' is a clonally propagated $F_3$ selection derived from intercrosses of the USDA ornamental pepper release '90C44', a selection from the heirloom tabasco-type pepper 'Royal Black', the bell-type peppers 'Summer Sweet 860' and 'Ariane' and squash-type pepper 'Tennessee Cheese'. The pedigree is complex (FIG. 1) and none of the parents were protected. '05C69-12' recombines many different characteristics from all of the different parents and does not resemble any single parent. For example plants of 'Tennessee Cheese' produce flattened fasciated immature green fruit that ripen to red on green foliaged plants; while plants of 'Royal Black' produce tabasco shape immature fruit that ripen to red on variegated green and purple foliaged plants; and plants of 'Ariane' and 'Summer Sweet 860' produce typical large 'bell' pepper shaped fruit which ripen to orange and red, respectively. '90C44' was derived from interbreeding a diverse collection of small-fruited pungent germplasm from India. Most of the seedlings in this cross had green to purple variegated foliage. '90C44' was unique among the progeny in having solid purple foliage. The genes for the black foliage of '05C69-12' were derived from intercrosses of '90C44' and 'Royal Black'. The genes for the orange mature fruit color of '05C69-12' were derived from 'Ariane'. The $F_3$ selection is descended from an intercross of parental lines exhibiting (1) prostrate growth habit with green foliage and orange tabasco type fruit and (2) upright growth habit, black foliage and immature black tabasco type fruit.

SUMMARY OF THE NEW PLANT

This application relates to a new and distinct pepper plant known as *Capisum annuum* L. '05C69-12'. The following characteristic is outstanding: When compared to all other pepper plants known to us, '05C69-12' has a unique contrasting mixed display of immature black and mature orange fruit, greenish black foliage and spreading indeterminate growth habit.

The following characteristics are useful in distinguishing this plant and can be useful for plant identification:

1. Plants produce greater than three basal shoots that grow upright forming a compact growth habit (47 cm height and 84 cm diameter).
2. Plants produce numerous small tabasco shaped (3.4 cm long, 1.2 cm wide at midpoint and 1.3 cm wide at the calyx) upright oriented solitary black fruits that mature orange.
3. Plants produce greenish black foliage.

BRIEF DESCRIPTION OF THE PHOTOGRAPHS

The accompanying photographs show typical characteristics of the new plant.

FIG. 1 shows the parentage of '05C69-12'.

FIG. 2 shows a mature plant of '05C69-12' in September 2007.

FIG. 3 shows mature orange and immature black fruit and greenish black leaves.

DESCRIPTION OF THE NEW PLANT

The following is a detailed description of the new plant, together with the plant's morphological characteristics. The characteristics of the plant were compared to the similar 'Ember' (Syngenta Seeds). The description is based upon plants grown in the field at Beltsville, Md. about 90 days post-transplanting.

'05C69-12' is a diploid (2n=2x=24) herbaceous annual. '05C69-12' has performed uniformly in multiple trials. Leaves and stems are glabrous and glossy. Leaves are simple, entire, symmetrical, and lanceolate with an apiculate tip. Mature leaves average 4.3 cm in length (range: 4.0 to 4.5 cm) and 2.1 cm in width (range: 2.0 to 2.2 cm). Petiole length averages 2.5 cm (range: 2.5 to 2.6 cm). Adaxial leaf surface is green (Royal Horticultural Society Colour Chart number 132C) mottled with black (Royal Horticultural Society Colour Chart number 202A) highlights. 'Ember' has similar shaped and colored leaves. 'Ember' leaves average 4.6 cm in length (range: 4.1 to 4.7 cm) and 2.2 cm in width (range: 2.1 to 2.4 cm).

'05C69-12' has a unique contrasting mixed display on the same aged plant of immature black (Royal Horticultural Society Colour Chart number 202A) and mature orange (Royal Horticultural Society Colour Chart number 25A) fruit. '05C69-12' fruits are tabasco shaped, solitary and borne upright. Fruits average 3.4 cm in length (range: 3.2 to 3.7 cm), 1.2 cm in width at the midpoint (range: 1.2 to 1.3 cm), and 1.3 cm in width at the calyx (range: 1.2 to 1.4 cm). The upright pedicels are 1.5 cm. There are approximately 375 fruit per plant and an average of 44 seed per fruit (range: 40 to 48). Fruit are extremely pungent. Since '05C69-12' is intended for ornamental applications, Scoville pungency units were not determined. Fruit of 'Ember' are similar in shape to '05C69-12' fruit but have different immature and mature fruit color. 'Ember' fruit are tabasco shaped and borne in clusters of 3 to 5. 'Ember' fruit average 3.0 cm in length (range: 2.8 to 3.4 cm), 0.8 cm in width at the midpoint (range: 0.7 to 0.8 cm), and 0.8 cm in width at the calyx (range: 0.7 to 0.9 cm). Immature 'Ember' fruit color is purple (Royal Horticultural Society Colour Chart number 79A) and mature fruit color is red (Royal Horticultural Society Colour Chart number 34A).

'05C69-12' plants produce greater than three basal shoots that grow upright forming a compact growth habit. Growth is indeterminate. Plants average 84 cm in diameter (range: 82 to 88 cm) and 47 cm in height (range: 45 to 49 cm). 'Ember' plants have a smaller height to diameter ratio (0.60) and average 36 cm in diameter (range: 34 to 39 cm) and 22 cm in height (range: 19 to 24 cm).

'05C69-12' flowers are self-compatible, hermaphroditic, pentamerous and hypogynous. The purple flowers (Royal Horticultural Society Colour Chart number 81A) average 2.7 cm in diameter (range: 2.5 to 2.9 cm) and have purple filaments and styles. Flowers of 'Ember' are similar.

Typical of *C. annuum,* '05C69-12' is a warm-season crop requiring minimum daytime temperatures of 18 to 21 C. Optimal growth is achieved at higher temperatures up to 32 C. Plants grow poorly in the 5 to 15 C range and are frost-susceptible. Like most peppers, '05C69-12' is field tolerant to most pests and diseases, e.g., Fusarium wilt, verticillium wilt, aphids, and mites, based on field reaction, not in controlled testing.

'05C69-12' has been asexually reproduced by vegetative shoot cuttings over successive generations since 2005. Over that period no off-type of '05C69-12' has been observed or reported to us. Thus it is concluded that '05C69-12' is stable and reproduced true to type in successive generations of asexual reproduction. Plants were propagated at Beltsville, Md. and Dearing, Ga.

References

Royal Horticultural Society. 1966. Royal Horticultural Society Colour Chart. Royal Hort. Soc., London, UK.

Stommel, J. R. and P. W. Bosland 2006. Pepper, Ornamental, *Capsicum annuum,* p. 561–599. In: Anderson, N. O. (ed.). Flower breeding and genetics: Issues, challenges and opportunities for the 21st century. Springer, Dordrecht, The Netherlands.

Stommel, J. R. and R. G. Griesbach. 1993. New ornamental *Capsicum* germplasm: Lines 90C40, 90C44, and 90C53. HortScience 28:858–859.

What is claimed is:

1. A new and distinct pepper plant known as '05C69-12' as described herein, illustrated and identified by the characteristics set forth above.

* * * * *

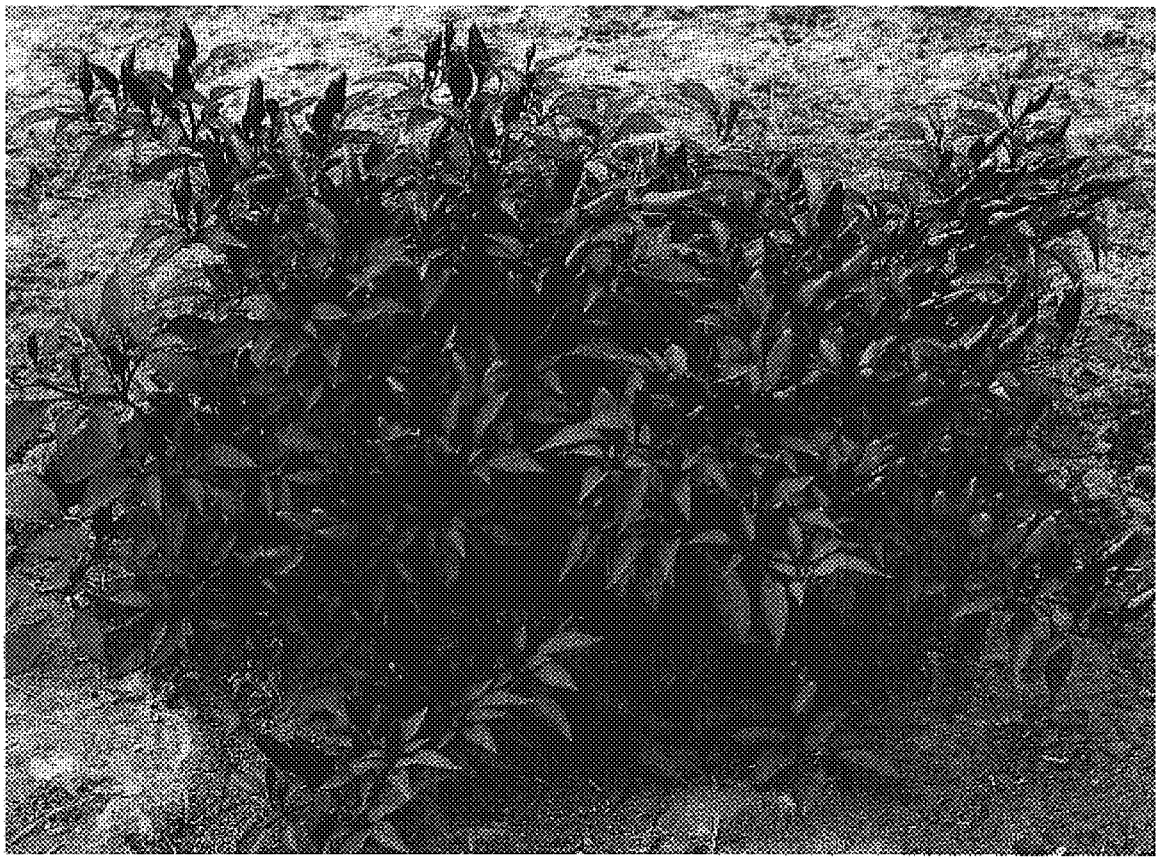

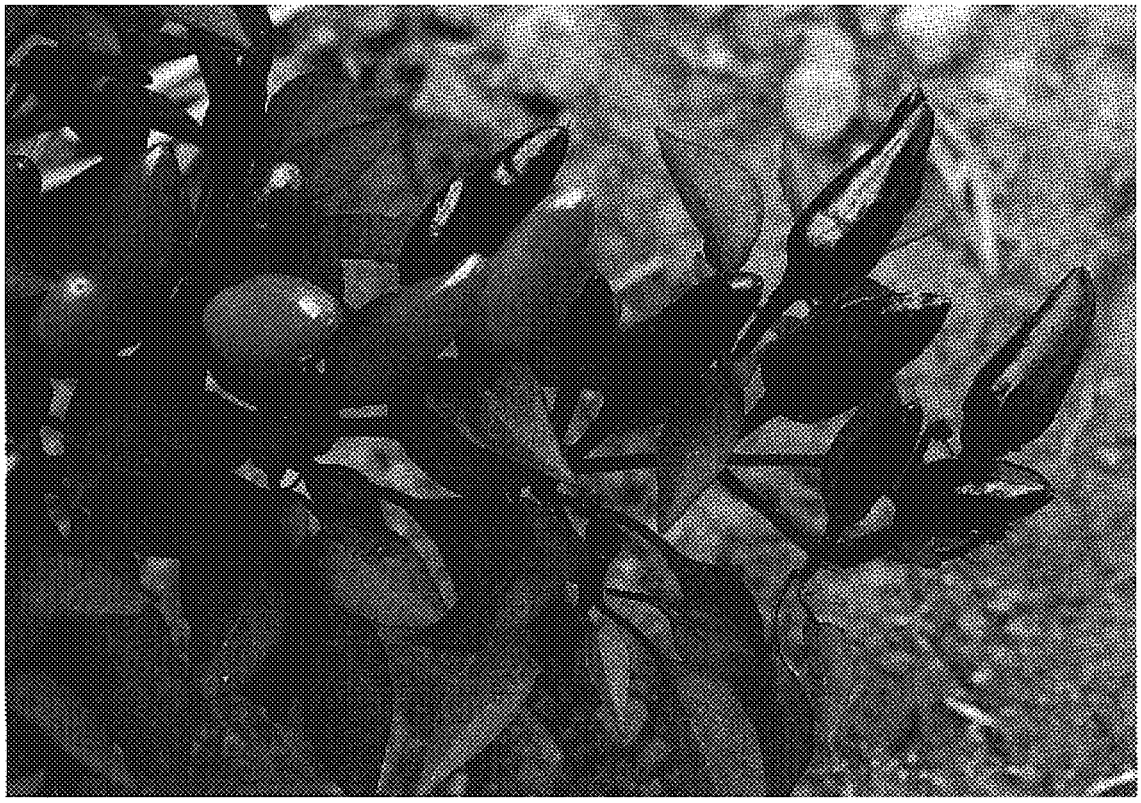

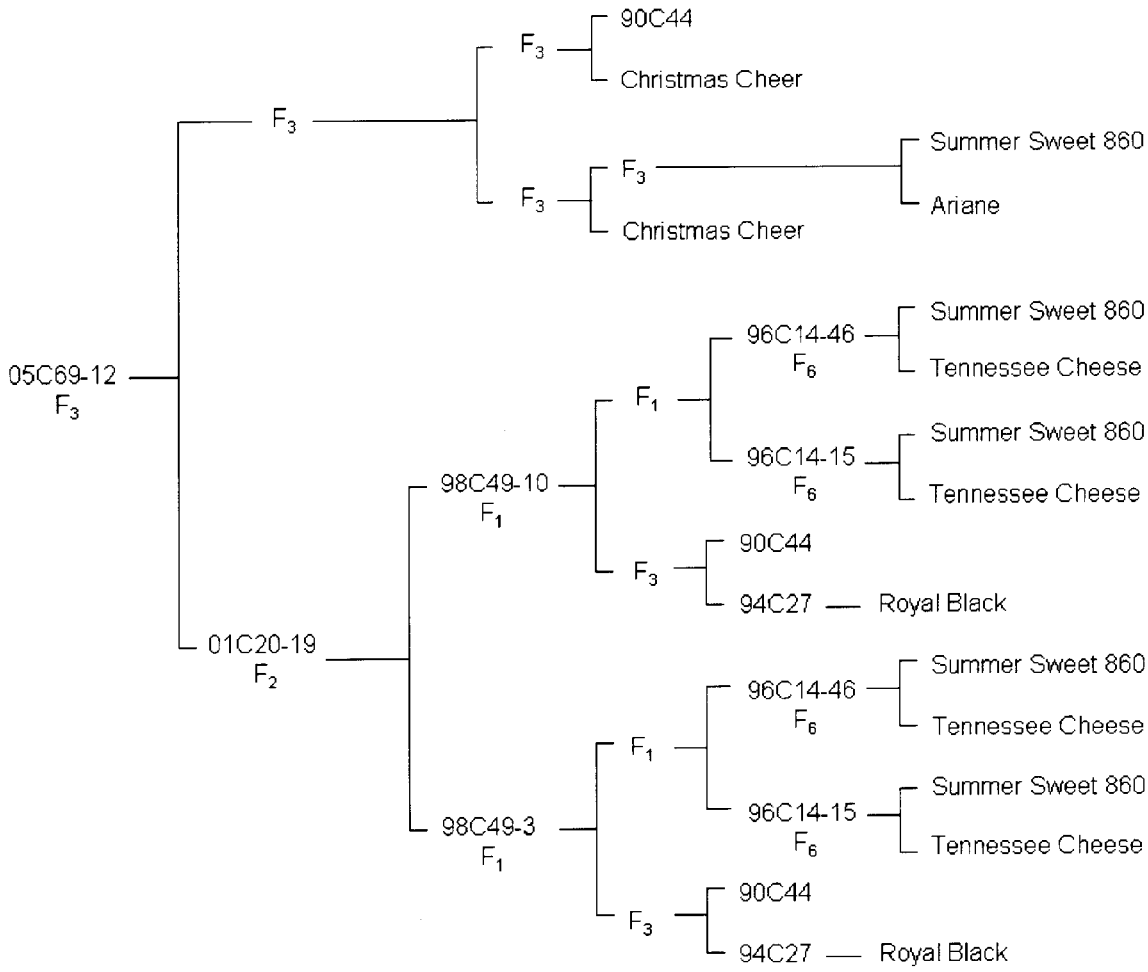
05C69-12
F3
F3
F3
90C44
Christmas Cheer
F3
F3
Summer Sweet 860
Ariane
Christmas Cheer
01C20-19
F2
98C49-10
F1
F1
96C14-46
F6
Summer Sweet 860
Tennessee Cheese
96C14-15
F6
Summer Sweet 860
Tennessee Cheese
F3
90C44
94C27
Royal Black
98C49-3
F1
F1
96C14-46
F6
Summer Sweet 860
Tennessee Cheese
96C14-15
F6
Summer Sweet 860
Tennessee Cheese
F3
90C44
94C27
Royal Black